(12) United States Patent
Roger

(10) Patent No.: US 7,371,261 B2
(45) Date of Patent: *May 13, 2008

(54) ACETABULAR COMPONENT OF TOTAL HIP REPLACEMENT ASSEMBLY

(75) Inventor: Gregory James Roger, New South Wales (AU)

(73) Assignee: Advanced Surgical Design & Manufacture Ltd., St. Leonards, New South Wales (AU)

( * ) Notice: Subject to any disclaimer, the term of this patent is extended or adjusted under 35 U.S.C. 154(b) by 375 days.

This patent is subject to a terminal disclaimer.

(21) Appl. No.: 10/781,860

(22) Filed: Feb. 20, 2004

(65) Prior Publication Data

US 2004/0225371 A1    Nov. 11, 2004

Related U.S. Application Data

(63) Continuation-in-part of application No. 09/926,684, filed on Mar. 4, 2002, now Pat. No. 6,712,857.

(51) Int. Cl.
*A61F 2/32* (2006.01)

(52) U.S. Cl. ................. 623/22.21; 623/22.39

(58) Field of Classification Search ............. 623/22.21, 623/22.24, 22.25, 22.26, 22.28
See application file for complete search history.

(56) References Cited

U.S. PATENT DOCUMENTS 3,813,699 A * 6/1974 Giliberty ................. 623/22.17
3,982,281 A * 9/1976 Giliberty ................. 623/22.24
4,892,551 A * 1/1990 Haber ...................... 623/23.17
5,009,665 A    4/1991 Serbousek et al. ............ 623/22
5,226,917 A * 7/1993 Schryver ................. 623/22.37
5,480,448 A * 1/1996 Mikhail ................... 623/22.24
5,725,589 A * 3/1998 Pfaff et al. ............... 623/22.29
6,248,132 B1 * 6/2001 Harris ..................... 623/22.15
6,475,243 B1 * 11/2002 Sheldon et al. .......... 623/22.28
6,610,097 B2 * 8/2003 Serbousek et al. ....... 623/22.24
6,712,857 B1 * 3/2004 Roger ..................... 623/22.21
6,811,569 B1 * 11/2004 Afriat et al. ............. 623/22.32
6,926,740 B2 * 8/2005 Lewis et al. .............. 623/22.28

FOREIGN PATENT DOCUMENTS

| DE | 3414514 A1 | 10/1985 |
|---|---|---|
| EP | 0142759 A2 | 5/1985 |
| EP | 0262379 A1 | 4/1988 |
| EP | 0613658 A1 | 9/1994 |
| EP | 0888759 A1 | 1/1999 |
| FR | 2630907 | 11/1989 |
| GB | 2159416 A | 12/1985 |
| WO | WO85/02535 | 6/1985 |
| WO | WO97/29698 | 8/1997 |

* cited by examiner

*Primary Examiner*—Ralph A. Lewis
(74) *Attorney, Agent, or Firm*—Jones Day

(57) ABSTRACT

A device for use in surgical procedures involving arthroplasty, the device including a bearing member at least partially receivable within a bone engaging member and a liner positioned at least partially between said bearing member and said bone engaging member.

31 Claims, 5 Drawing Sheets

ACETABULAR COMPONENT OF TOTAL HIP REPLACEMENT ASSEMBLY

This is a continuation-in-part of U.S. application Ser. No. 09/926,684 filed Mar. 4, 2002, now U.S. Pat. No. 6,712,857.

FIELD OF THE INVENTION

The present invention generally relates to a method and apparatus for use in surgical procedures involving arthroplasty. More specifically, it relates to a prosthetic socket portion of a joint replacement assembly, and a method for its insertion during arthroplasty. Particular reference is drawn to the apparatus in the form of an acetabular portion of a total hip replacement assembly.

BACKGROUND ART

The inclusion of the following description of the prior art is not an admission that the prior art is part of the common general knowledge in Australia.

It is well known to use prosthetic joint replacements in patients with various kinds of disorders affecting the joints, including degenerative disorders, such as severe osteoarthritis.

Over the years, a vast array of materials have been developed and utilised in the construction and manufacture of such prostheses. This is partly because the knowledge base regarding materials, and relevantly biocompatible materials, has been growing. It is also because, despite technological advances, there are a continuing number of complications associated with joint replacement prostheses with which surgeons and patients must grapple. As a result, surgeons and other inventors in the field have had, and are still challenged with, an ongoing quest to improve on the ease of insertion of the prostheses, to reduce the incidence of long and short term complications associated with using them, and to improve on the longevity of both the bio-prosthetic interface and the prostheses themselves.

Since the present invention refers specifically to a socket portion of a joint replacement assembly, and particularly refers to an acetabular component of a total hip replacement assembly, it is the latter which the following discussion briefly addresses.

The hip joint is comprised of the head of the femur articulating with the acetabulum. The acetabulum is generally cotyloidal in shape, and is often referred to as a "cup".

One of the first designs for the acetabular component of the hip joint, which was developed around 1960, was a hemisphere of metal internally lined with a plastics hemisphere, with the latter acting as the articulation surface. The metal was cemented into the bone and the liner was either pressed into the metal cup during the arthroplasty procedure, or was incorporated into the prosthesis during manufacture. In some later designs, the preferred method of securing the prosthesis was to screw it to the bone. However, while providing good fixation, screws have been found to lead to serious complications in the hip and are now not well regarded. Consequently, some of the more recent developments in acetabular prostheses have focused on new designs for their bone contacting surfaces. For example, some acetabular prostheses have been manufactured with a self-cutting thread on their bone contacting surface, while others have relied on press fitting along with cement, or a combination of surface roughening and hydroxyapatite.

In addition to considerable variation in the designs of the outer, or bone contacting, surfaces of acetabular prostheses, however, much research has been done in order to provide improved means of engaging the head of the femur (or prosthesis thereof). Forte (U.S. Pat. No. 5,062,853), for example, describes a particular construction for the inner aspect of the acetabular prosthesis which is particularly well adapted to receive and engage a corresponding prosthetic head of a femur.

Nevertheless, while prosthetic hip joint replacements have been shown to be incredibly beneficial for patients who require them, there are still a number of problems associated with their insertion for which further developments in the method and apparatus would be advantageous. The present invention is, most specifically, aimed at improving the bone contacting surface of acetabular prostheses, and therefore addresses many of the problems raised above.

DESCRIPTION OF THE INVENTION

In a first aspect, the present invention consists in a device for use in surgical procedures involving arthroplasty, the device including a socket member having a first surface and a second bone engaging surface, the first surface including at least a bearing surface adapted to receive a counter-component of a joint, and the bone engaging surface including a first portion having a shape, and at least a second portion having a different shape to that of the first portion.

In a second aspect, the present invention consists in a method of inserting a device according to the first aspect during an arthroplasty procedure, the method including the steps of:

a) bringing a surface of an appropriate joint orientation determining means into apposition with the exposed surface of the socket portion of a joint;

b) manipulating the joint orientation determining means so that the correct angular orientation for a socket portion of a joint replacement assembly is determined;

c) forming a hole into the bone adjacent the joint orientation determining means with a hole forming means, using said joint orientation determining means as a guide;

d) removing the joint orientation determining means from apposition with said exposed surface;

e) using the hole formed in step (c) as a guide, reaming an appropriately shaped and sized portion of bone from the bone forming the socket portion of the joint to a desired depth, thereby creating a reamed surface of bone;

f) bringing the bone engaging surface of a device according to the first aspect of the invention into contact with the reamed surface of bone; and g) securing the device to the bone.

It is also noted that the use of Image Guided and Robotic Guidance surgical tools will also allow the accurate placement of the implant according to pre-operative planning and anatomical landmarks.

The device according to this invention may be used in a range of arthroplasty procedures, but is of particular applicability when used as a replacement for the acetabular component of a hip joint. By virtue of the nature of its function, preferred embodiments disclose that the socket member, as a whole, has a cotyloidal configuration with a longitudinal axis. The first surface of the socket member includes a bearing surface having a radius of curvature which is adapted to receive the counter-component of a joint, such as the head of the femur (or prosthesis thereof) in a hip joint. The socket member is, according to this invention, defined by a bone engaging surface. In accordance with its name, the bone engaging surface is adapted to engage a bony surface comprising a portion of the joint which the device is intended to replace, such as the acetabulum in a hip joint.

Preferred embodiments of the invention disclose that the bone engaging surface of the socket member comprises at least a first and a second portion. In such embodiments, the first portion extends away from a circumferential join with the first surface of the socket member, and the second portion extends away from a circumferential join with the first portion to an extremity.

In further preferred embodiments, as the first portion extends away from its join with the first surface of the socket member, its cross-sectional diameter may decrease at a first rate. In such embodiments, the rate of change in cross-sectional diameter may be linear such that the first portion has a frusto-conical shape. In alternative embodiments, the rate of change may be logarithmic, exponential or may follow any other mathematical expression. In yet further alternative embodiments, the rate of change may itself change from one to another of these mathematical expressions as the first portion extends away from its join with the first surface.

Similarly, as the second portion extends away from its join with the first portion, its cross-sectional diameter may decrease at a second different rate to that of the cross-sectional diameter of the first portion. In preferred embodiments, the rate of change will comply with a mathematical expression which will cause the second portion to form a spherical section, and preferably, a hemi-section or a smaller section still. In alternative embodiments, the discussion of the mathematical expressions according to which the rate of change may comply from the paragraph above is also applicable to the rate of change for the cross-sectional diameter of the second portion.

As indicated above, however, in a preferred embodiment the first portion of the bone engaging surface is frusto-conical, while the second portion comprises a spherical section. Construction of the device according to either of these aspects of the invention, therefore, envisages the bone engaging surface of the socket member including any one of a plurality of combinations of portions having these, and other additional, shapes.

In some such embodiments of the invention, for example, the bone engaging surface includes a plurality of portions of different shapes, wherein at least one portion is frusto-conical, and another, comprises a spherical section; while in other embodiments, the bone engaging surface includes only two portions, each having one of the latter shapes. Indeed, embodiments of the invention wherein these two portions alone comprise the bone engaging surface are preferred. Consequently, the foregoing description outlines preferred structural combinations of the frusto-conical portion and portion comprising a spherical section for the bone engaging surface of the socket member.

In preferred embodiments, the bone engaging surface of the socket member is substantially hemispherical, having its rounded extremity formed by the portion of the bone engaging surface comprising a spherical section. In other words, in these particular embodiments, the frusto-conical portion of the bone engaging surface is oriented so that its smallest cross-sectional diameter meets, circumferentially, with the hemisphere formed by the portion comprising a spherical section; and its largest cross-sectional diameter meets, circumferentially, with the first surface of the socket member.

In alternative embodiments, the bone engaging surface comprises a frusto-conical portion, a portion comprising a spherical section, and a planar portion or a portion comprising a section of a larger sphere than the latter. Such embodiments disclose a similar configuration to that described in the preceding paragraphs. However, while the extremity of the bone engaging surface still has a substantially hemispherical surface, a portion of that surface is essentially planar.

As indicated earlier, the scope of this invention is not limited to the embodiments just described. There are multiple variations for the construction of the bone engaging surface having a plurality of portions, each with unique shapes, which fall within its scope. However, it is noteworthy that the incorporation of a bone engaging surface having a combination of a frusto-conical portion and portion comprising a spherical section may contribute considerably to the functionality and securability of the socket member.

In replacing a socket portion of a joint, the fixation of the socket member must be able to withstand rotational and other movement influencing forces created during articulation of the joint. While the means used to secure the socket member to the bone (see below) will be of substantial importance in this regard, having a frusto-conical shape for a portion of the bone engaging surface of the invention is also of particular value, as such a shape has excellent side rotational stabilising capacity.

In addition, such a shape helps to ensure that any compressive forces which the socket member applies to the bone during, for example, weight-bearing, is desirably distributed: with a frusto-conical shape, compression of the bone will be greatest at the largest cross-sectional diameter of the frusto-conical portion, namely, around the first surface of the socket member. The latter will, when the socket member has been inserted according to this invention, be located near the surface of the bone. It is desirable for the greatest compressive force which the socket member applies to the bone to be distributed at this location. This is because, if the greatest compression occurs in deeper regions of the bone, for example, those regions adjacent the extremity of the bone engaging surface of the socket member, then the surface bone is protected from stress and tends to weaken.

The capacity of a socket member according to this invention to distribute such compressive forces desirably is further augmented by the presence of a portion comprising a spherical section near or at the extremity of the bone engaging surface. In preferred embodiments, the bone engaging surface of the socket member, despite being comprised of a plurality of portions each having unique shapes, is continuous, in that the meeting loci of these portions are not interrupted, or constructed, by a sharp edge or a 'step'. When the portion comprising a spherical section is at the extremity of the bone engaging surface it acts as a further means to ensure that no such edge or step is in contact with the surrounding bone. The value of ensuring as much, especially near the extremity of the bone engaging surface, is that an edge-like or step-like protrusion would, during the application of weight-bearing compressive forces, act as a stress riser on the bone. For the reasons already outlined, among others, this is not desirable.

Preferred embodiments also disclose that a bearing surface is located at the first surface of the socket member. Such a bearing surface, has the capacity to receive the counter-component of a joint such as the head of the femur (or prosthesis thereof) in a hip joint.

In some such embodiments of the invention, the first surface of the socket member is comprised of a relatively planar surface into which the bearing surface forms an indent. Because the bearing surface receives the counter-component of the joint, the materials used in the construction of the invention warrant discussion: while there are no particular limitations on the materials to be used in the manufacture of the socket member, it is replacing a bony component of a joint, and must, therefore, have similar characteristics in terms of strength and resilience. Various metals, as well as ceramics, or carbon fibre may all be appropriate. As an integral component of the socket member, the bearing surface will also be made of such a material. However, since this surface of the socket member represents the articulating surface of the joint, it is desirable to use a high-wear resistance material such as polyethylene or ceramics. Accordingly, in preferred embodiments of the invention, a shell being made of polyethylene, or similar appropriate material, and having a shape which corresponds with the bearing surface is machine fitted to the latter. Note, however, that although machine fitting provides for a tighter fit and a convenient form of manufacture, it is not a requisite component of this invention that the shell be fitted by machine. Indeed, any appropriate method of fitting the shell, including for example, by known methods of clipping it into position, falls within the scope of this invention.

It is further noteworthy that as the bearing surface comes under load, there may be relative movement, or micromotion, between the shell and the bearing surface of the socket member to which it is fitted. This can generate wear particles. In order to render less likely such generation, preferred embodiments of the invention disclose that an interface between the bearing surface of the socket member and the shell is surface-coated with a material, such as titanium nitrate or titanium carbide. Alternatively, the surface may be roughened in order to reduce relative motion, whereby the two materials "key in" to each other.

Additionally disclosed is a method for inserting a socket member according to the invention during an arthroplasty procedure. Although not required in many cases, it may initially be necessary for the surgeon to perform a small hemispherical ream into the bone forming the socket portion of the joint. It may be appropriate to do so in cases where this part of the joint has undergone severe pathological degeneration.

Nevertheless, whether or not the decision is made to perform the small hemispherical ream, the method generally includes the steps of:

a) bringing a surface of an appropriate joint orientation determining means into apposition with the exposed surface of the socket portion of the joint. For the purposes of this disclosure, a "joint orientation determining means" refers to an appropriate device which can be used to determine the correct orientation for a replacement prosthesis;

b) manipulating the joint orientation determining means so that the correct angular orientation for a socket portion of a joint replacement assembly is determined.

Such determination is critical, both for ensuring the best alignment and also for finding a position which provides the least likelihood of dislocation. Determination of the correct angular orientation may be achieved by having reference to appropriate anatomical landmarks, by simple visualisation, or with whatever method is preferred by the surgeon;

c) forming a hole into the bone adjacent the joint orientation determining means with a hole forming means, such as a drill bit, using said joint orientation determining means as a guide. In preferred embodiments of the invention, the joint orientation determining means is pre-prepared with a hole designed to receive the hole forming means. In alternative embodiments, it may not be;

d) removing the joint orientation determining means from apposition with the exposed surface of bone;

e) using the hole formed in (c) as a guide, reaming an appropriately shaped and sized portion of bone from the bone forming the socket portion of the joint to a desired depth, thereby creating a reamed surface of bone. In preferred embodiments, the reamed surface should extend to a depth slightly beyond the depth attained, according to this invention, by the extremity of the bone engaging surface of a fully inserted socket member.

f) bringing the bone engaging surface of a socket member according to the invention into contact with the reamed surface of bone; and g) securing the socket member to the bone. In preferred embodiments, the socket member is press fit, and not threaded. While a socket member having a thread is not outside the scope of this invention, the press fit solution is preferred as it significantly decreases the technical complexity of insertion. As explained in (e) above, when the socket member is fully inserted, preferred embodiments disclose that there should be a small space between the extremity of the bone engaging surface and the reamed surface of bone. This space provides room to allow for a small amount of subsidence of the socket member when it is subjected to compressive forces, for example, during weight-bearing.

Reinforced fixation of the socket member in the correct position may additionally be achieved by cement, by a combination of roughening and hydroxyapatite, or by any other appropriate means.

The socket member, according to this invention, is now ready to receive the counter-component of the joint, or a prosthesis thereof.

More specifically, in cases where a socket member according to the invention will be used to replace the acetabular portion of a hip joint, similar commentary regarding the steps above is appropriate, but in summary, the method includes the following:

a) bringing a convex surface of a hemispherical cup (an appropriate joint determining means for hip joint arthroplasty) into apposition with the exposed surface of the acetabulum;

b) manipulating the hemispherical cup so that the correct angular orientation for an acetabular portion of a total hip replacement assembly is determined;

c) forming a hole into the bone adjacent the hemispherical with a hole forming means, such as a drill bit, using said hemispherical cup as a guide;

d) removing the hemispherical cup from apposition with the exposed surface of the acetabulum;

e) using the hole drilled in (c) as a guide, reaming an appropriately sized frusto-conical portion of bone from the acetabulum to a desired depth, thereby creating a reamed surface of bone;

f) bringing a socket member according to this invention into contact with the reamed surface of bone; and g) securing the socket member to the bone.

The socket member is now ready to receive the head of the femur, or a prosthesis thereof.

In accordance with this latter description, pertaining to a method for inserting a device according to the invention in an arthroplasty procedure on the hip joint, a further aspect to the invention is disclosed:

In a further aspect, the present invention consists in a method of inserting a device according to the first aspect during an arthroplasty procedure involving the hip joint, wherein the bone engaging surface is comprised of a first frusto-conical portion and at least a second portion, wherein the second portion includes a spherical section, the method including the steps of:

a) bringing a convex surface of a hemispherical cup into apposition with the exposed surface of the acetabulum;

b) manipulating the hemispherical cup so that the correct angular orientation for an acetabular portion of a hip replacement assembly is determined;

c) forming a hole in the acetabulum with a hole forming means, using the hemispherical cup as a guide;

d) removing the hemispherical cup from apposition with said exposed surface of acetabulum;

e) using the hole drilled in (c) as a guide, reaming an appropriately sized frusto-conical portion of bone from the acetabulum to a desired depth, thereby creating a reamed surface of bone;

f) bringing a device according to this aspect of the invention into contact with the reamed surface of bone; and g) securing the device to the bone.

A significant advantage of the present invention is that in the event that an error is made while carrying out step (e), and the ream is found to be in the wrong direction, the option is still available to then use a hemispherical reamer to slightly enlarge the reamed surface of bone, with minimal extra bone resection. In this instance, it will be possible to still position a hemispherical socket member against the reamed hemispherical surface and secure it to the bone. Thus, the present invention additionally offers a satisfactory avenue for dealing with initial errors of alignment in reaming the appropriately sized frusto-conical portion of bone.

As noted above, the device of the present invention may be a one-piece unit or optionally comprise two pieces. In the latter, the device may include a first component that sits within a reamed section of bone and receives a cup component therewithin. The first component is typically made from a biocompatible metal and the cup component from a polyethylene of ceramic material. The cup component receives a counter component of a joint.

Typically, the first component is secured to the bone of a patient by screws, thus requiring screw holes to receive the screws. When the polyethylene or ceramic cup component is placed within the first component and the device subjected to the fluid pressures experienced during walking, micromovement between the two components may occur. This may lead to the production of debris that can migrate through the screw holes within the first component and penetrate the bone, resulting in bone loss.

In a further aspect of the invention, therefore, there is provided a device for use in a surgical procedure involving arthroplasty, the device including a bearing member at least partially received within a recess of a bone engaging member and a liner positioned at least partially between said bearing member and said bone engaging member to substantially cover at least one bone securing means of said bone engaging member.

In another aspect, the present invention comprises a liner for an arthroplasty device, said liner at least partially positionable between a bearing member and a bone engaging member of the arthroplasty device to substantially cover at least one bone securing means of the bone engaging member.

The bearing member may comprise a first surface to receive a counter component of a joint and a second surface that is engageable with said liner. The bone engaging member may have a liner engaging surface and a bone engaging surface.

The first surface of the bearing member may comprise a relatively planar surface into which is formed an indent to receive a ball portion of a joint.

The second surface of the bearing member may form a circumferential join with the first surface and extend away from said circumferential join to define a substantially hemispherical or frustoconical portion.

The bone engaging member typically also has a relatively planar surface into which is formed the recess, said recess defined by the liner engaging surface and said planar surface forming a rim around the recess. The recess receives the bearing member of the device.

The liner of the device preferably substantially conforms with the contour of the liner engaging surface of the bone engaging member.

The at least one bone securing means may comprise at least one and preferably a plurality of screw holes through which screws may threaded. In use, the bone engaging member is positioned appropriately within a reamed portion of bone and the screws threaded through the holes and into the bone of the patient to secure the bone engaging member to the bone.

The liner typically fully covers the screw hole(s) and the screw(s) when the bone engaging member is secured to the bone of the patient. In a preferred embodiment, at least a portion of the liner extends beyond the liner engaging surface of the bone engaging member. Typically, the portion of the liner that extends beyond the liner engaging surface comprises a lip member that engages the rim of the bone engaging member. In this embodiment, the liner fully seals the space between the bearing member and the bone engaging member thereby reducing micromovement between the two and the build up of wear debris when the device is in use. By fully sealing the space between the two components, any wear debris is also prevented from migrating into the bone via the screw holes of the bone engaging member.

Preferably, the liner is made from a biocompatible material including titanium. The bearing member is typically made from a polyethylene or ceramic material and the bone engaging member is preferably made from a biocompatible metal. Optionally, the bone engaging member may be made from a graded material including a functionally graded or biologically graded material, or reinforced hydroxyapatite.

The liner of the device preferably has a diameter of less than 1 mm and more preferably less than 0.5 mm. This embodiment is particularly advantageous in that the liner is sufficiently thin so as to not significantly increase the thickness of the device and so as to deform and cold weld to the bone engaging member of the device.

In a still further aspect, there is provided a method of inserting a device during an arthroplasty procedure, the device including a bearing member at least partially receivable within a recess of the bone engaging member and a liner positioned at least partially between said bearing member and said bone engaging member to substantially cover at least one bone securing means of the bone engaging member, said method comprising:

(a) positioning the bone engaging member within a suitably reamed portion of bone of a patient;

(b) fixing said bone engaging member to the bone of the patient via said at least one bone securing means;

(c) positioning the liner adjacent or in engagement with said bone engaging member;

(d) positioning the bearing member within the recess of the bone engaging member and securing the bearing member to the bone engaging member such that the liner is positioned therebetween.

Typically, the liner is secured to a liner engaging surface of the bone engaging member prior to positioning of the bearing member. In this regard, the liner may be cold welded to the bone engaging member.

The bone engaging member is typically fixed to the bone of a patient by a screw or a plurality of screws. In this regard, the liner is preferably positioned such that it fully covers said screw or plurality of screws.

The bearing member may be secured to the bone engaging member by press fit.

Typically, the device of the present invention replaces an acetabular portion of a joint including a hip joint of a patient.

BRIEF DESCRIPTION OF THE DRAWINGS

By way of example, preferred embodiments of the invention are described with reference to the accompanying drawings in which:

FIG. 3a is a perspective view of a socket member according to the preferred embodiment of the invention illustrated in FIG. 2a;

FIG. 3b is a cross-sectional view of the socket member of FIG. 3a;

FIG. 4b is a cross-sectional view of the socket member of FIG. 4a;

PREFERRED MODE OF CARRYING OUT THE INVENTION

Figure 1:
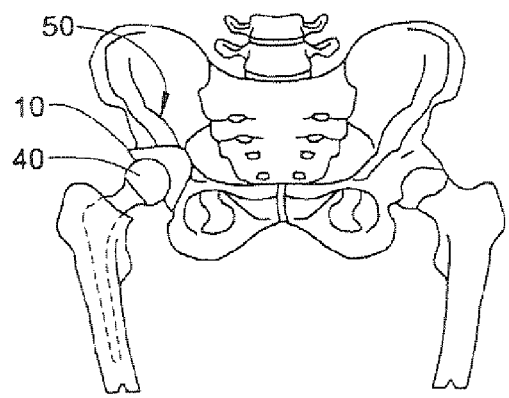
FIG. 1 is a schematic representation of a prosthetic total hip replacement assembly, as inserted, following arthroplasty to the right hip.
Figure 2A:
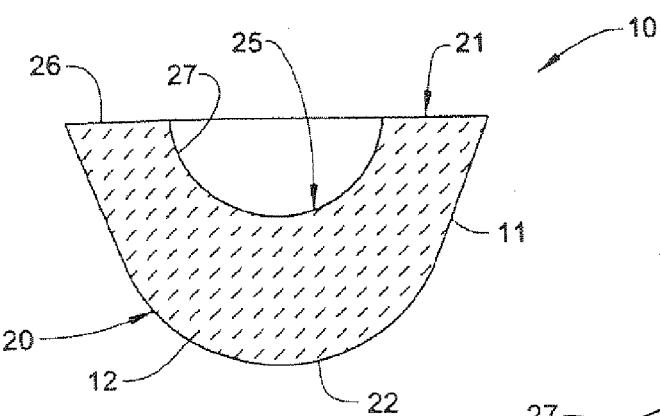
FIG. 2a is a cross-sectional view of a socket member according to a preferred embodiment of the invention.
Figure 2B:
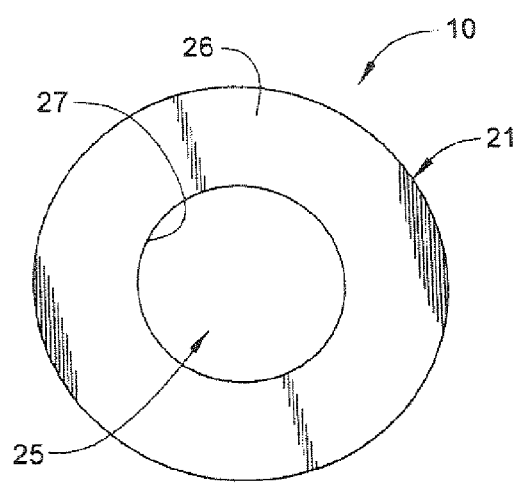
FIG. 2b is a diagrammatic representation of a top view of the socket member in FIG. 2a, illustrating the first surface of that socket member.
Figure 3A:
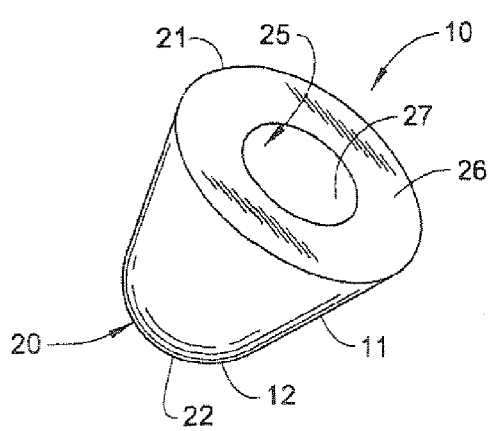
Figure 3B:
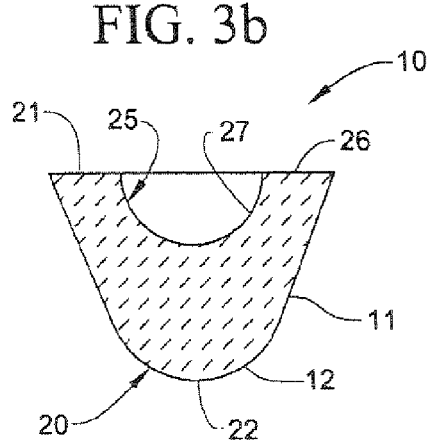
Figure 4A:
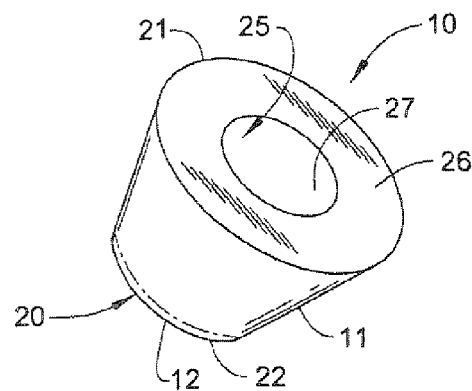
FIG. 4a is a perspective view of a socket member according to another embodiment of this invention.
Figure 4B:
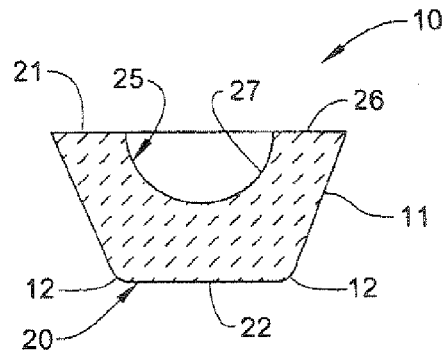
Figure 5A:
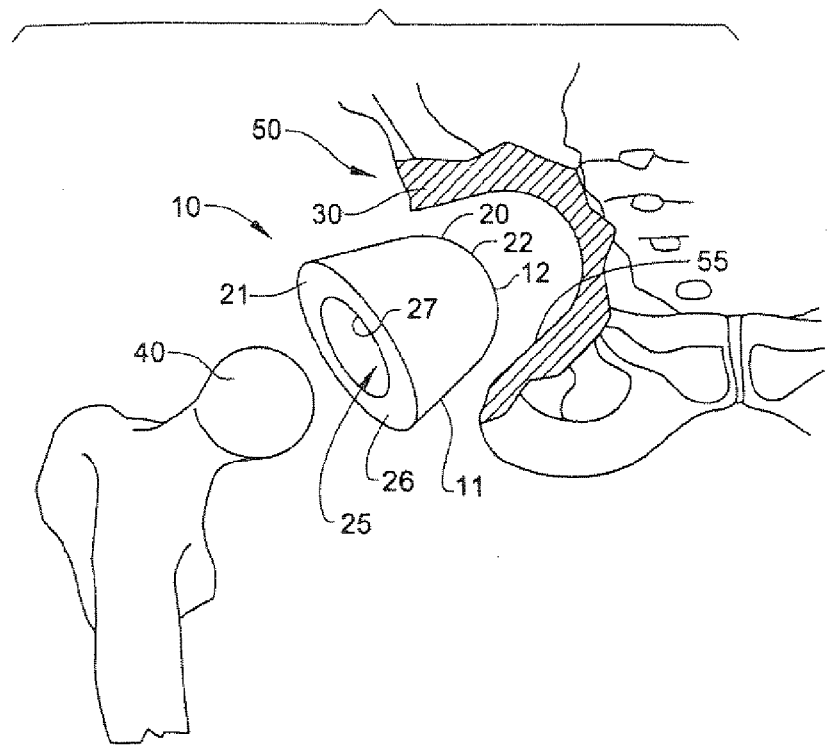
FIG. 5a is an exploded perspective view illustrating the relative positions of the reamed surface of the acetabulum, the socket member according to a preferred embodiment of the invention, and the head of the femur (or prosthesis thereof), as they are each about to be inserted into the right hip.
Figure 5B:
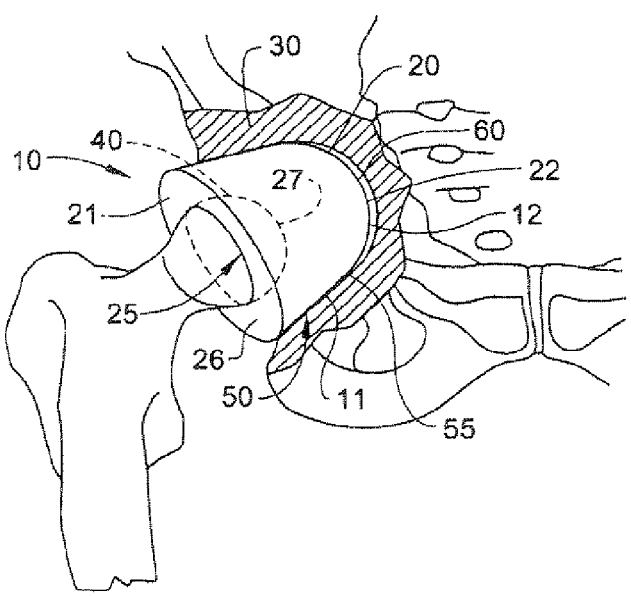
FIG. 5b is a perspective view illustrating the componentry shown in FIG. 5a as correctly inserted into the right hip.
Figure 6:
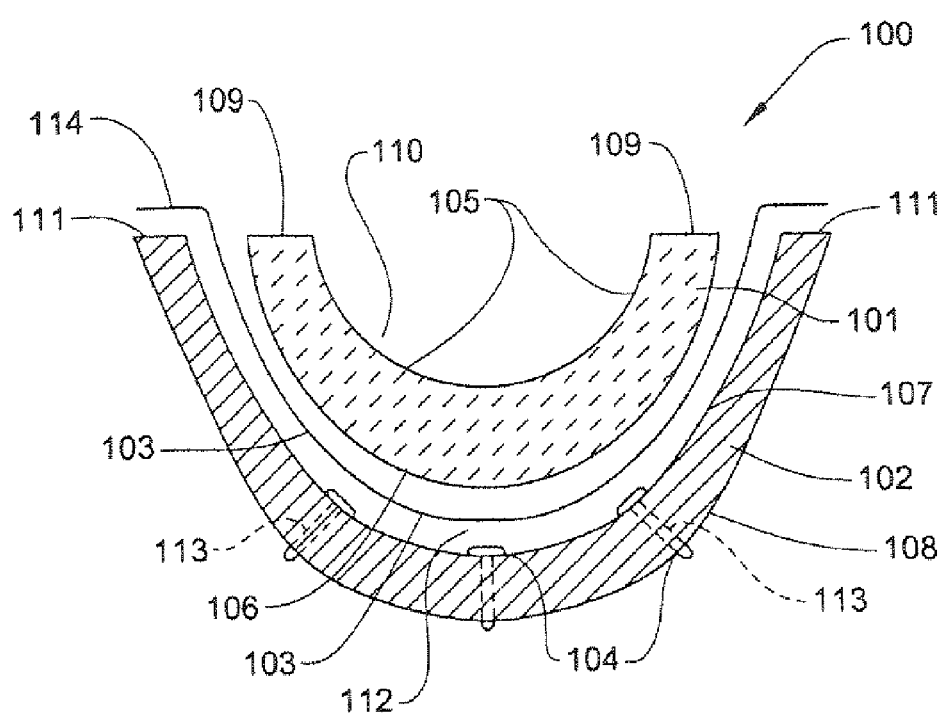
FIG. 6 is a cross-sectional view of a device according to a further aspect of the invention.
Figure 7:
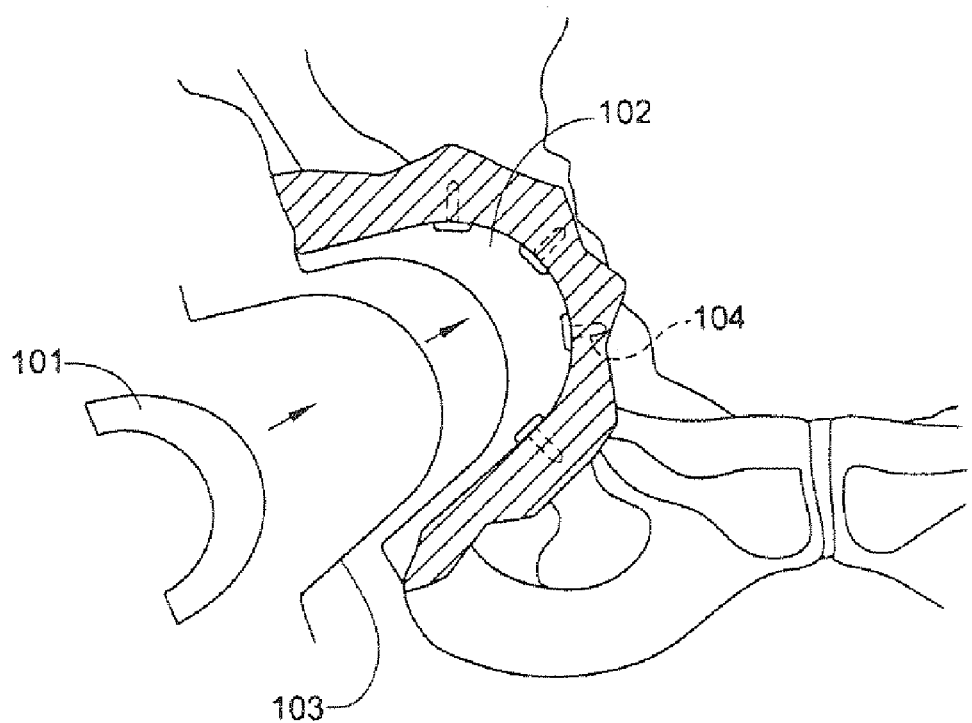
FIG. 7 is a perspective view of positioning of the components of the device depicted in FIG. 6 during a hip arthroplasty procedure.

The device according to this invention may be used in a range of arthroplasty procedures, but is of particular applicability to arthroplasty procedures involving the hip joint (see FIG. 1).

The socket member 10 has a bone engaging or contacting surface 20 that is comprised of a first portion which is frusto-conical 11, and a second portion comprising a spherical section 12. Consequently, the foregoing description outlines preferred structural combinations of the frusto-conical portion 11 and portion comprising a spherical section 12 for the bone contacting surface 20 of the socket member 10.

The bone contacting surface 20 of the socket member 10 extends away from the socket member's first surface 21 in such a way that the cross-sectional diameter of the bone contacting surface 20 (in a plane substantially perpendicular to the longitudinal axis) diminishes at one rate for the frusto-conical portion 11, and diminishes at a second different rate for the second portion comprising a spherical section 12 to a rounded extremity 22. In other words, the frusto-conical portion 11 of the bone contacting surface 20 is oriented so that its smallest cross-sectional diameter meets, circumferentially, with the hemispherical section formed by the portion comprising a spherical section 12; and its largest cross-sectional diameter meets, circumferentially, with the first surface 21 of the socket member 10.

As indicated earlier, the scope of this invention is not limited to the embodiments just described. There are multiple variations for the construction of the bone contacting surface 20 having a plurality of portions, each with unique shapes, which fall within its scope. However, as noted in the description of the invention the incorporation of a bone contacting surface 20 having a combination of a frusto-conical portion 11 and portion comprising a spherical section 12 may contribute considerably to the functionality and securability of the socket member 10.

In replacing a socket portion of a joint, the fixation of the socket member 10 must be able to withstand rotational and other movement forces created during articulation of the joint. Having a frusto-conical shape for a portion 11 of the bone contacting surface 20 of the invention is also of particular value, as such a shape has excellent side rotational stabilising capacity.

In addition, such a shape helps to ensure that any compressive forces which the socket member 10 applies to the bone during, for example, weight-bearing, is desirably distributed: with a frusto-conical shape 11, compression of the bone will be greatest at the largest cross-sectional diameter of the frusto-conical portion 11, namely, at around the join with the first surface 21 of the socket member 10. The latter will, when the socket member 10 has been inserted according to this invention, be located near the surface of the bone 30. It is desirable for the greatest compressive force which the socket member 10 applies to the bone 30 to be distributed at this location. This is because, if the greatest compression occurs in deeper regions of the bone 30, for example, those regions adjacent the extremity 22 of the bone contacting surface 20 of the socket member 10, then the surface bone 30 is protected from stress and tends to weaken.

The capacity of a socket member 10 according to this invention to distribute such compressive forces desirably is further augmented by the presence of a portion comprising a spherical section 12 near or at the extremity 22 of the bone contacting surface 20. In preferred embodiments, the bone contacting surface 20 of the socket member 10, despite being comprised of two portions each having unique shapes (11 and 12 respectively), is continuous, in that the meeting loci of these portions 11 and 12 are not interrupted, or constructed, by a sharp edge or a 'step'. When the portion comprising a spherical section 12 is at the extremity 22 of the bone contacting surface 20 it acts as a further means to ensure that no such edge or step is in contact with the surrounding bone 30. The value of ensuring as much, especially near the extremity 22 of the bone contacting surface 20, is that an edge-like or step-like protrusion would, during the application of weight-bearing compressive forces, act as a stress riser on the bone. For the reasons already outlined, among others, this is not desirable.

The bearing surface 25 is located at the first surface 21 of the socket member 10. Such a bearing surface 25, has the capacity to receive the counter-component of a joint such as the head of the femur 40 (or prosthesis thereof) in a hip joint. In fact, the first surface 21 of the of the socket member 10 is comprised of a relatively planar annular surface 26 into which the bearing surface 25 forms an indent.

While there are no particular limitations on the materials to be used in the manufacture of the socket member 10, it is replacing a bony component of a joint, and must, therefore, have similar characteristics in terms of strength and resilience. As already explained, various metals, as well as ceramics, or carbon fibre may all be appropriate. As an integral component of the socket member 10, the bearing surface 25 will also be made of such a material. However, since this surface 25 of the socket member 10 represents the articulating surface of the joint, it is desirable to use a material of high wear resistance such as polyethylene or ceramics. Accordingly, a shell 27 being made of polyethylene, or similar appropriate material, and having a shape which corresponds with the bearing surface 25 is, in the depicted embodiment, machine fitted to the latter. However, although machine fitting provides for a tighter fit and a convenient form of manufacture, it is not a requisite component of this invention that the shell 27 be fitted by machine. Indeed, any appropriate method of fitting the shell 27, including for example, by known methods of clipping it into position, falls within the scope of this invention.

In addition, as the bearing surface 25 comes under load, there may be relative movement, or micro-motion, between the shell 27 and the bearing surface 25 of the socket member 10 to which it is fitted. This can generate wear particles. In order to render less likely such generation, the interface between the bearing surface 25 of the socket member 10 and the shell 27 is surface-coated with a material, such as titanium nitrate or titanium carbide.

Also disclosed is a method for inserting a socket member 10 according to the invention as a prosthetic replacement for the acetabular portion of a hip joint (see FIG. 1). Although not required in many cases, it may initially be necessary for the surgeon to perform a small hemispherical ream into the acetabulum 50. It may be appropriate to do so in cases where this part of the joint has undergone severe pathological degeneration. Nevertheless, whether or not the decision is made to perform the small hemispherical ream, the method generally includes the steps of:

a) bringing a convex surface of a hemispherical cup (not shown) (an appropriate joint determining means for hip joint arthroplasty) into apposition with the exposed surface of the acetabulum 50;

b) manipulating the hemispherical cup (not shown) so that the correct angular orientation for an acetabular portion of a total hip replacement assembly is determined. Such determination is critical, both for ensuring the best alignment and also for finding a position which provides the least likelihood of dislocation. Determination of the correct angular orientation may be achieved by having reference to appropriate anatomical landmarks, by simple visualisation, or with whatever method is preferred by the surgeon;

c) forming a hole (not shown) into the bone 30 adjacent the hemispherical cup (not shown) with a drill bit (not shown), using said hemispherical cup as a guide. The hemispherical cup is normally pre-prepared with a hole designed to receive the drill bit;

d) removing the hemispherical cup (not shown) from apposition with the exposed surface of the acetabulum 50;

e) using the hole drilled in (c) as a guide, reaming an appropriately sized frusto-conical portion of bone from the acetabulum to a desired depth, thereby creating a reamed surface 55 of bone 30. The reamed surface 55 should extend to a depth slightly beyond the depth attained, according to this invention, by the extremity 22 of the bone contacting surface 20 of a fully inserted socket member 10.

f) bringing a socket member 10 according to this invention into contact with the reamed surface 55 of bone 30; and g) securing the socket member 10 to the bone 30. In the depicted embodiment, the socket member 10 is press fit, and not threaded. As explained in (e) above, when the socket member 10 is fully inserted, there should be a small space 60 between the extremity 22 of the bone contacting surface 20 and the reamed surface 55 of bone 30. This space 60 provides room to allow for a small amount of subsidence of the socket member 10 when it is subjected to compressive forces, for example, during weight-bearing.

Reinforced fixation of the socket member 10 in the correct position may additionally be achieved by cement, by a combination of roughening and hydroxyapatite, or by any other appropriate means.

The socket member 10, according to this invention, is now ready to receive the head of the femur 40, or a prosthesis thereof.

In a further aspect of the invention, device 100 comprises a bearing member 101 that is received in a recess of a bone engaging member 102. The device also has a liner 103 positioned between the bearing member 101 and the bone engaging member 102 to substantially cover bone securing means 104 of the bone engaging member 102.

The bearing member comprises a first surface 105 to receive a counter component of a joint and a second surface 106 that is engageable with the liner 103. The bone engaging member has a liner engaging surface 107 and a bone engaging surface 108.

The first surface 105 of the bearing member comprises a relatively planar surface portion 109 into which is formed an indent 110 to receive a ball portion of a joint.

The bone engaging member 102 also has a relatively planar surface portion 111 into which is formed the recess 112, said recess 112 defined by the liner engaging surface 107 and said planar surface portion 111 forming a rim around the recess. The recess receives the bearing member 101.

The liner 103 substantially conforms with the contour of the liner engaging surface 107 of the bone engaging member 102.

The bone securing means 104 comprises at least one and preferably a plurality of screw holes through which screws 113 are threaded. In use, the bone engaging member 102 is positioned appropriately within a reamed portion of bone and the screws 113 threaded through the holes and into the bone of the patient to secure the bone engaging member 102 to the bone.

The liner typically fully covers the screw holes and the screws 113 when the bone engaging member 102 is secured to the bone of the patient. In a preferred embodiment, at least a portion 114 of the liner 103 extends beyond the liner engaging surface 107 of the bone engaging member 102. Typically, the portion 114 of the liner 103 that extends beyond the liner engaging surface comprises a lip member that engages the rim of the bone engaging member. In this embodiment, the liner fully seals the space between the bearing member 101 and the bone engaging member 102 thereby reducing micromovement between the two and the build up of wear debris when the device is in use. By fully sealing the space between the two components, any wear debris is also prevented from migrating into the bone via the screw holes of the bone engaging member.

Preferably, the liner is made from a biocompatible material including titanium. The bearing member is typically made from a polyethylene or ceramic material and the bone engaging member is preferably made from a biocompatible metal. Optionally, the bone engaging member may be made from a graded material including a functionally graded or biologically graded material, or reinforced hydroxyapatite.

In use, the bone engaging member 102 is positioned within a suitably reamed portion of bone of a patient. The bone engaging member 102 is then fixed to the bone of the patient via screws 113. The liner 103 is then positioned adjacent or in engagement with said bone engaging member 102 and the bearing member 101 positioned within the recess 112 of the bone engaging member 102. The bearing member 101 is then secured to the bone engaging member 102 such that the liner 103 is positioned therebetween.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A device for use in surgical procedures involving arthroplasty, the device comprising:
    a socket member comprising:
        a first surface adapted to receive a counter component of a joint, and
        a bone engaging surface comprising:
            a first surface portion that extends away from a circumferential join with the first surface; and
            a second surface portion that extends away from a the first surface portion to an extremity;
    wherein the first surface portion is configured such that a cross-sectional diameter of the first surface portion decreases at a first rate as the first surface portion extends away from the circumferential join with the first surface, and the second surface portion is configured such that a cross-sectional diameter of the second surface portion decreases at a second rate, the second rate being different from the first rate, and
    wherein the first surface portion and the second surface portion are arranged relative to each other such that the bone engaging surface is devoid of a step or an edge at a meeting loci of the first surface portion and the second surface portion.

2. The device of claim 1, wherein the bone engaging surface being devoid of a step or a corner prevents the application of undue stress to the surrounding bone.

3. The device of claim 1, when used as a replacement for the acetabular component of a hip joint.

4. The device of claim 1, wherein the first rate of decrease in cross-sectional diameter of the socket member is linear.

5. The device of claim 1, wherein the second rate of decrease in cross-sectional diameter of the socket member is logarithmic or exponential.

6. The device of claim 1, wherein the second rate of decrease in cross-sectional diameter of the socket member varies as the second surface portion extends away from a line of meeting with the first surface portion and the second surface portion.

7. The device of claim 1, wherein the first surface portion is defined by a frustoconical section of the socket member and the second surface portion is defined by a spherical section of the socket member.

8. The device of claim 7, wherein the frusto-conical section of the socket member is oriented so that its smallest cross-sectional diameter meets, circumferentially, with a hemisphere formed by the spherical section and its largest cross-sectional diameter meets, circumferentially, with the first surface of the socket member.

9. The device of claim 1, wherein the socket member is cotyloidal in configuration with a longitudinal axis.

10. The device of claim 1, wherein the first surface of the socket member comprises a relatively planar surface into which the bearing surface forms an indent.

11. The device of claim 1 wherein the socket member is made from any one of the group comprising metals, ceramics, or carbon fibre.

12. The device of claim 1, wherein the bearing surface of the socket member is made from a material of higher wear resistance relative the remaining material of the socket member.

13. The device of claim 12, wherein the bearing surface is made from polyethylene or a ceramic material.

14. The device of claim 1, wherein a shell of polyethylene having a shape which corresponds with the bearing surface is fitted to the bearing surface.

15. The device of claim 14, wherein an interface formed between the bearing surface of the socket member and the shell is surface-coated with titanium nitrate or titanium carbide.

16. A device for use in surgical procedures involving arthroplasty, the device comprising:
    a bone engaging member configured to be secured to a bone with at least one bone securing means;
    a bearing member configured to be at least partially received within a recess of the bone engaging member; and
    a liner configured to be positioned at least partially between the bearing member and the bone engaging member to substantially cover the at least one bone securing means of the bone engaging member;
    wherein the bone securing member comprises:
        a liner engaging surface; and
        a bone engaging surface, comprising:
            a first surface portion that extends away from a circumferential join with the liner engaging surface; and
            a second surface portion that extends away from a the first surface portion to an extremity;
    wherein the first surface portion is configured such that a cross-sectional diameter of the first surface portion decreases at a first rate as the first surface portion extends away from the circumferential join with the first surface, and the second surface portion is configured such that a cross-sectional diameter of the second surface portion decreases at a second rate, the second rate being different from the first rate, and
    wherein the first surface portion and the second surface portion are arranged relative to each other such that the bone engaging surface is devoid of a step or an edge at a meeting loci of the first surface portion and the second surface portion.

17. The device of claim 16, wherein the bearing member has a first surface configured to receive a counter component of a joint and a second surface that is configured to be engageable with the liner.

18. The device of claim 17, wherein the first surface of the bearing member comprises a relatively planar surface into which is formed an indent configured to receive a ball portion of a joint.

19. The device of claim 17, wherein the second surface of the bearing member forms a circumferential join with the first surface and extends away from the circumferential join to define a substantially hemispherical or frustoconical portion.

20. The device of claim 16, wherein the bone engaging member has a relatively planar surface into which is formed the recess, the recess defined by the liner engaging surface, the planar surface forming a rim around the recess.

21. The device of claim 16, wherein the at least one bone securing means of the bone engaging member comprises at least one screw hole to receive a screw for securing the bone engaging member to the bone of a patient.

22. The device of claim 21, wherein the liner substantially conforms with the contour of the liner engaging surface of the bone engaging member and covers the at least one screw hole of the bone engaging member.

23. The device of claim 22, wherein at least a portion of the liner extends beyond the liner engaging surface of the bone engaging member.

24. The device of claim 23, wherein said portion of the liner that extends beyond the liner engaging surface comprises a lip member that engages the rim of the bone engaging member.

25. The device of claim 21, wherein when the device is in use, the liner prevents the migration of wear debris to the bone via the at least one screw hole of the bone engaging member.

26. The device of claim 25, wherein when the device is in position within a patient, the liner also reduces relative movement between the bearing member and the bone engaging member thereby reducing the amount of wear debris produced as a result of said relative movement.

27. The device of claim 16, wherein the liner is made from a biocompatible material including titanium.

28. The device of claim 16, wherein the bearing member is made from a polyethylene or ceramic material.

29. The device of claim 16, wherein the bone engaging member is made from a metal or plastics material.

30. The device of claim 16, wherein the liner has a thickness of less than 1 mm.

31. The device of claim 30, wherein the liner has a diameter of less than 0.5 mm.

* * * * *